United States Patent
Liu et al.

(10) Patent No.: US 7,947,734 B2
(45) Date of Patent: May 24, 2011

(54) SUBSTITUTED PARA-TRIFLUOROMETHYL PHENYLATE COMPOUNDS AND ITS PREPARATION AND USE THEREOF

(75) Inventors: Changling Liu, Shenyang (CN); Huiwei Chi, Shenyang (CN); Miao Li, Shenyang (CN); Zhinian Li, Shenyang (CN); Dongliang Cui, Shenyang (CN); Yanmei Luo, Shenyang (CN); Jing Yuan, Shenyang (CN)

(73) Assignees: Sinochem Corporation, Beijing (CN); Shenyang Research Institute of Chemical Industry, Shenyang (CN)

( * ) Notice: Subject to any disclaimer, the term of this patent is extended or adjusted under 35 U.S.C. 154(b) by 717 days.

(21) Appl. No.: 11/912,411

(22) PCT Filed: Jun. 15, 2006

(86) PCT No.: PCT/CN2006/001337
§ 371 (c)(1),
(2), (4) Date: Oct. 24, 2007

(87) PCT Pub. No.: WO2007/000098
PCT Pub. Date: Jan. 4, 2007

(65) Prior Publication Data
US 2008/0188468 A1    Aug. 7, 2008

(30) Foreign Application Priority Data
Jun. 28, 2005   (CN) .......................... 2005 1 0046765

(51) Int. Cl.
C07C 69/54      (2006.01)
C07C 251/48     (2006.01)
A01N 43/54      (2006.01)
A01N 43/88      (2006.01)

(52) U.S. Cl. ................... 514/535; 514/539; 514/229.2; 514/269; 560/60; 544/65; 544/319

(58) Field of Classification Search .............. 544/65, 544/319; 560/60; 514/229.2, 269, 535, 539
See application file for complete search history.

(56) References Cited

U.S. PATENT DOCUMENTS
5,679,676 A * 10/1997 Kruger et al. .............. 514/229.2

FOREIGN PATENT DOCUMENTS
JP        4-182461        *   6/1992

OTHER PUBLICATIONS
Hayase et al., CAPLUS 118:59429, 1993.*

* cited by examiner

*Primary Examiner* — Deepak Rao
(74) *Attorney, Agent, or Firm* — Smith, Gambrell & Russell, LLP

(57) ABSTRACT

The invention relates to substituted para-trifluoromethyl phenyl ether compounds and its preparation and use thereof especially. The substituted para-trifluoromethyl phenyl ether compounds of the invention having general formula (I):

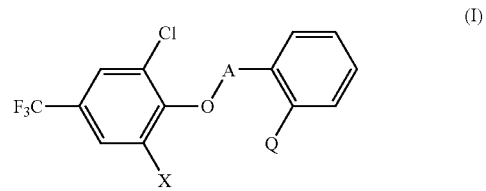

The substitutes see Description.

The compounds of present invention have broad-spectrum activity, and may be used to control diseases in all sorts of plants caused by oomycete, basidiomycete, ascomycete pathogens and deuteromycete, and it may also provide good control efficacy at very low dosage because of the high activity. The compounds of the invention have good insecticidal activity and have good activity against many pests, especially for Carmine spider mite. The compounds are fit for synthetical control against many kinds of pests.

8 Claims, No Drawings

SUBSTITUTED PARA-TRIFLUOROMETHYL PHENYLATE COMPOUNDS AND ITS PREPARATION AND USE THEREOF

This application is a 371 of PCT/CN2006/001337 filed Jun. 15, 2006.

FIELD OF THE INVENTION

The invention relates to insecticide and fungicide, especially to substituted para-trifluoromethyl phenyl ether compounds and its preparation and use thereof.

BACKGROUND OF THE INVENTION

The introduction of the fluoro atom can double the activity of compounds because the fluoro atom has good simulation, electronic effect, block effect, penetration and so on. Some new pesticides containing fluoro have come forth recently, the proportion of new pesticides gets higher and higher.

Methoxyacrylate compounds are known with bioactivity. They were disclosed in many patents, for example EP335519, U.S. Pat. No. 4,829,085, U.S. Pat. No. 4,914,128, U.S. Pat. No. 5,145,980, U.S. Pat. No. 5,157,144, U.S. Pat. No. 5,334,748, U.S. Pat. No. 5,395,854, U.S. Pat. No. 6,653,258, US2004029944, WO2003087032 and so on, many pesticides have been commercialized, the structures and names of some commercialized pesticides are as follows.

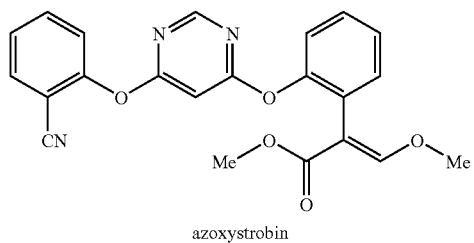

azoxystrobin

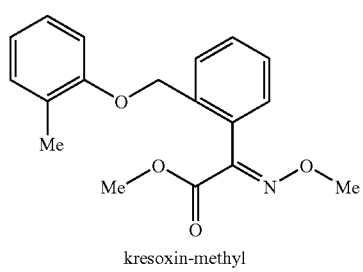

kresoxin-methyl

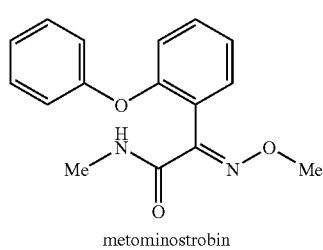

metominostrobin

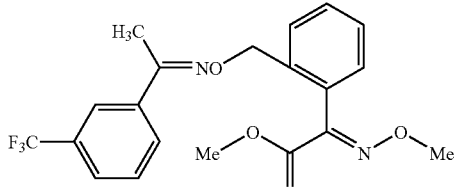

trifloxystrobin

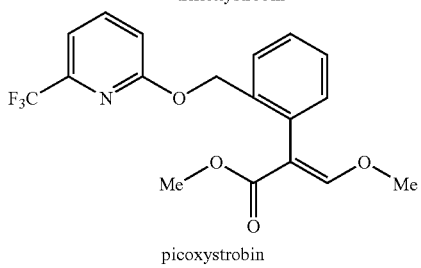

picoxystrobin

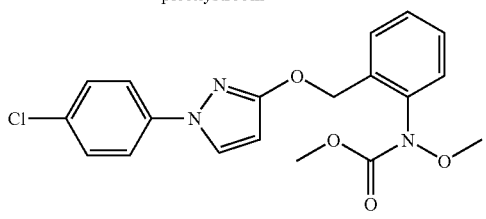

pyraclostrobin

Though there have been many patents and commercialized pesticides, the substituted para-trifluoromethyl phenyl ether compounds of the invention have not been published especially.

THE SUMMARY OF INVENTION

The aim of invention is to provide substituted para-trifluoromethyl phenyl ether compounds with biological activity against all sorts of plant diseases and insect pests at very low dosage and be applied to the agriculture to control the diseases and insects in plant.

Detailed description of the invention is as follows.

The present invention offered substituted para-trifluoromethyl phenyl ether compounds having general formula (I):

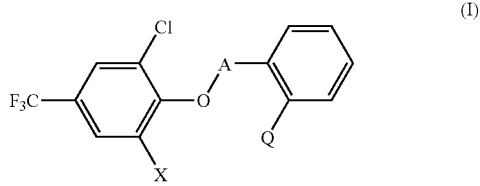

(I)

Wherein Q is selected from $Q_1$, $Q_2$, $Q_3$, $Q_4$ or $Q_5$ as follows:

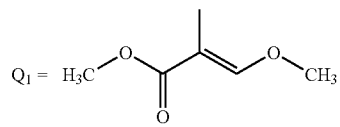

$Q_2 =$ 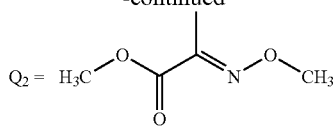

$Q_3 =$ 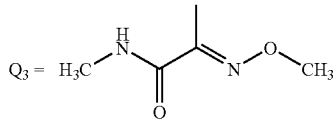

$Q_4 =$ 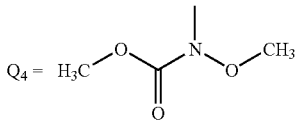

$Q_5 =$ 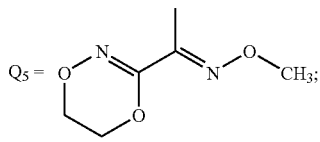

A is selected from $CH_2$ or

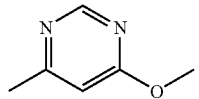

When $A =$ 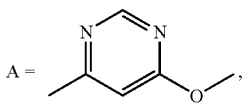, its 4-position is linked with oxygen, the oxygen of 6-position is linked with benzene, $Q=Q_1$;

X is selected from H, halo, CN, $NO_2$, $C_1$-$C_{12}$alkyl, $C_2$-$C_{12}$alkenyl, $C_2$-$C_{12}$alkynyl, $C_1$-$C_{12}$haloalkyl, $C_1$-$C_{12}$alkoxy, $C_1$-$C_{12}$alkylthio, $C_1$-$C_{12}$alkylsulfonyl, $C_1$-$C_{12}$alkylcarbonyl, $C_1$-$C_{12}$alkoxyl $C_1$-$C_{12}$alkyl, $C_1$-$C_{12}$alkoxylcarbonyl, $C_1$-$C_{12}$alkoxylcarbonyl $C_1$-$C_{12}$alkyl, $C_1$-$C_{12}$haloalkoxyl $C_1$-$C_{12}$alkyl, or group may be substituted by any other group: amino $C_1$-$C_{12}$alkyl, aroxyl, aryl $C_1$-$C_{12}$alkoxy, aryl, heteroary, aryl$C_1$-$C_{12}$alkyl, heteroaryl$C_1$-$C_{12}$alkyl or heteroaryl$C_1$-$C_{12}$alkoxyl;

and stereoisomer.

The preferred compounds of general formula (I) of this invention are:

Q is selected from $Q_1$, $Q_2$, $Q_3$, $Q_4$ or $Q_5$; A is selected from $CH_2$ or

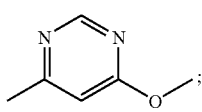

When $A =$ 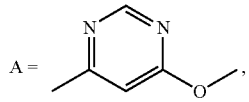, the 4-position of pyrimidine is linked with oxygen, the oxygen of 6-position is linked with benzene, $Q=Q_1$; X is selected from H, halo, CN, $NO_2$, $C_1$-$C_6$alkyl, $C_2$-$C_6$alkenyl, $C_2$-$C_6$alkynyl, $C_1$-$C_6$haloalkyl, $C_1$-$C_6$alkoxy, $C_1$-$C_6$alkylthio, $C_1$-$C_6$alkylsulfonyl, $C_1$-$C_6$alkylcarbonyl, $C_1$-$C_6$alkoxyl $C_1$-$C_6$alkyl, $C_1$-$C_6$alkoxylcarbonyl, $C_1$-$C_6$alkoxylcarbonyl $C_1$-$C_6$alkyl, $C_1$-$C_6$haloalkoxyl $C_1$-$C_6$alkyl, or group may be substituted by any other group: amino $C_1$-$C_6$alkyl, aroxyl, aryl $C_1$-$C_6$alkoxy, aryl, heteroaryl, aryl$C_1$-$C_6$alkyl, heteroaryl$C_1$-$C_6$alkyl or heteroaryl$C_1$-$C_6$alkoxyl;

Further more, the preferred compounds of general formula (I) of this invention are:

Q is selected from $Q_1$, $Q_2$, $Q_3$, $Q_4$ or $Q_5$; A is selected from $CH_2$ or

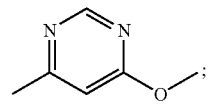;

When $A =$ 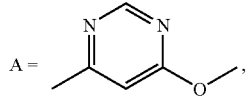, the 4-position is linked with oxygen, the oxygen of 6-position is linked with benzene, $Q=Q_1$; X is selected from H, halo, CN, $NO_2$, $C_1$-$C_6$alkyl, $C_2$-$C_6$alkenyl, $C_2$-$C_6$alkynyl, $C_1$-$C_6$haloalkyl, $C_1$-$C_6$alkoxy, $C_1$-$C_6$alkylthio, $C_1$-$C_6$alkylsulfonyl, $C_1$-$C_6$alkylcarbonyl, $C_1$-$C_6$alkoxyl $C_1$-$C_6$alkyl, $C_1$-$C_6$alkoxylcarbonyl, $C_1$-$C_6$alkoxylcarbonyl $C_1$-$C_3$alkyl, $C_1$-$C_3$haloalkoxyl $C_1$-$C_3$alkyl, or group may be substituted by any other group: amino $C_1$-$C_3$alkyl, or group is substituted or unsubstituted by any other group: phenyl, phenoxy, benzyl or benzyloxy.

Even more preferred compounds of formula (I) of this invention are:

Q is selected from $Q_1$, $Q_2$, $Q_3$ or $Q_4$; A is selected from $CH_2$ or

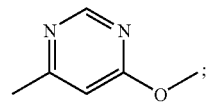;

When $A =$ 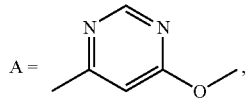, the 4-position of pyrimidine is linked with oxygen, the oxygen of 6-position is linked with benzene, Q=$Q_1$; X is selected from H, Cl, Br, F, CN, or $C_1$-$C_3$alkyl.

The following is the meaning of terms in the general formula (I):

Halogen or halo is meant to include fluoro, chloro, bromo and iodo.

The alkyl includes either straight or branched chain alkyl such as methyl, ethyl, propyl, isopropyl and tert-butyl.

The haloalkyl refers to straight or branched chain alkyl, in which hydrogen atom may be all or partly substituted with halogen, such as chloromethyl, dichloromethyl, trichloromethyl, fluoromethyl, difluoromethyl, trifluoromethyl.

The alkoxy refers to straight or branched chain alkyl, which is linked to the structure by oxygen atom.

The haloalkoxy refers to straight or branched chain alkoxy, in which hydrogen atom may be all or partly substituted with halogen, such as chloromethoxy, dichloromethoxy, trichloromethoxy, fluoromethoxy, difluoromethoxy, trifluoromethoxy, chlorofluoromethoxy.

The alkenyl refers to a straight or branched chain, having double bonds at any position such as vinyl or allyl. Substituted alkenyl includes arylvinyl which is substituted at any position with any group.

The alkynyl refers to a straight or branched, having triple bonds at any position. Such as ethynyl, propynyl. Substituted alkynyl includes arylethynyl which is substituted at any position with any group.

The aryl and aryl in arylalkyl, arylalkenyl, arylalkynyl, aryloxy, aryloxyalkyl include phenyl and naphthyl.

The hetero aryl in this invention refers to five member ring or six member ring containing one or many N, O, S hetero atom. Such as pyridine, furan, pyrimidine, pyrazine, pyridazine, triazine, quinoline or benzofuran.

The so called "substituted" is selected from alkyl, alkoxy, haloalkyl, haloalkoxy, halo, $NO_2$ or CN etc.

Because of the C=C and C=N link to different substituted group, the compounds of the invention may form geometrical isomer (the different isomers are respectively expressed with Z and E). Z isomer and E isomer and their mixture in any proportion are included in the invention.

The present invention is explained by the following compounds in table 1, but without being restricted thereby.

TABLE 1

(I)

| NO | A | X | Q |
|----|-----|-----|-----|
| 1 | $CH_2$ | H | $Q_1$ |
| 2 | $CH_2$ | Cl | $Q_1$ |
| 3 | $CH_2$ | $CH_3$ | $Q_1$ |
| 4 | $CH_2$ | H | $Q_2$ |
| 5 | $CH_2$ | Cl | $Q_2$ |
| 6 | $CH_2$ | $CH_3$ | $Q_2$ |
| 7 | $CH_2$ | H | $Q_3$ |
| 8 | $CH_2$ | Cl | $Q_3$ |
| 9 | $CH_2$ | $CH_3$ | $Q_3$ |
| 10 | $CH_2$ | H | $Q_4$ |
| 11 | $CH_2$ | Cl | $Q_4$ |
| 12 | $CH_2$ | $CH_3$ | $Q_4$ |
| 13 | $CH_2$ | H | $Q_5$ |

TABLE 1-continued (I)

| NO | A | X | Q |
|----|-----|-----|-----|
| 14 | $CH_2$ | Cl | $Q_5$ |
| 15 | $CH_2$ | $CH_3$ | $Q_5$ |
| 16 | 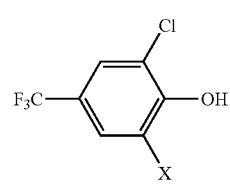 | H | $Q_1$ |
| 17 | 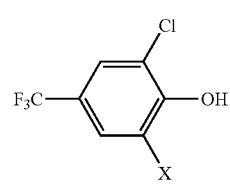 | Cl | $Q_1$ |
| 18 | 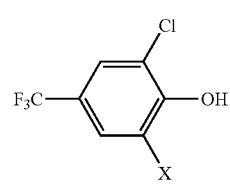 | $CH_3$ | $Q_1$ |
| 19 | $CH_2$ | F | $Q_1$ |
| 20 | $CH_2$ | $OCH_3$ | $Q_1$ |
| 21 | $CH_2$ | CN | $Q_1$ |

The present invention also includes preparation of compounds having formula I. It can be prepared by substituted phenol compounds there was no these two words having general formula II with halomethylbenzene having general formula III at the present of base in organic solvent:

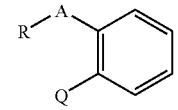

(II)

(III)

Wherein: R is leaving group, chosen from halogen such as Cl, Br or iodo. Other groups are as defined above.

The following is the reaction of preparation of compounds having formula I:

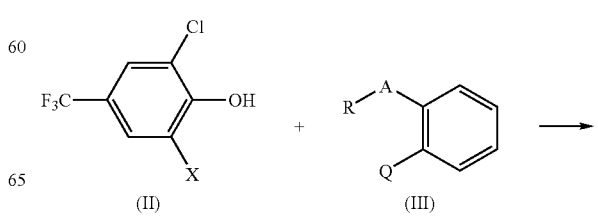

-continued

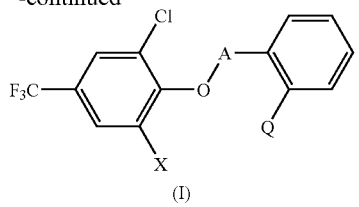

(I)

The proper solvent mentioned may be selected from tetrahydrofuran, acetonitrile, toluene, xylene, benzene, DMF, DMSO, acetone or butanone and so on.

The proper base mentioned may be selected from potassium hydroxide, sodium hydroxide, sodium carbonate, potassium carbonate, sodium bicarbonate, triethylamine, pyridine, sodium hydride, sodium methoxide, sodium ethoxide, potassium or sodium tert-butoxide and so on.

The proper temperature mentioned is from room temperature to boiling point of solvent, generally 20~100° C.

The reaction may be finished after 30 minutes-20 hours, generally 1-10 hours.

The substituted phenol compounds of the general formula (II) can be bought or prepared according to known methods, refer to U.S. Pat. No. 4,548,640.

The compounds of the general formula III can be prepared according to known methods, refer to U.S. Pat. No. 4,723,034, U.S. Pat. No. 5,554,578.

The compounds having the general formula I of present invention have broad-spectrum fungicidal activity, and may be used to control diseases in all sorts of plants caused by oomycete, basidiomycete, ascomycete pathogens and deuteromycete, and it may also provide good control efficacy at very low dosage because of the high activity. The compounds have good activity against diseases such as grape downy mildew, rice sheath blight, rice blast, tomato early blight, tomato late blight, wheat rust, wheat leaf blotch, wheat powdery mildew, wheat root rot, wheat glume blotch root rot, wheat leaf rust, cucumber powdery mildew, cucumber anthracnose, cucumber downy mildew, cucumber grey mold, especially for powdery mildew.

To our surprise, the compounds of the invention have good insecticidal activity, and have good activity against many pests such as armyworm, diamondback moth and aphids, Carmine spider mite and cluex pipiens pallens, especially for Carmine spider mite. The compounds are fit for synthetical control against all kinds of pests.

The compounds of the invention have better biological activity than commercial pesticide such as kresoxin-methyl by biological activity test.

The present invention also provides a composition of insecticides and fungicides, the active ingredients of the composition are the compounds having general formula (I), wherein the active ingredients being present in a total amount of 0.1 to 99% by weight.

The present invention, further more provides preparation method of the said composition thereon. The compounds of general formula (I) and their carrier are mixed. The said composition may be a single component compound or mixture of compounds with several components.

The carrier in the invention accords to the requirements is easy to apply to the sites being to be treated its confecting with active component. For example, the sites could be plant, seed or soil convenient for store, transport or operation. The carrier could be solid or liquid, including the liquid which usually turns from gas condition under pressure. And the carriers which are used to confect insecticidal, bactericidal composition are applied.

Suitable solid carriers include natural and synthetic clays and silicates, for example diatomaceous earths, talcs, magnesium aluminium silicates, aluminium silicates (kaoling), montmorillonites and micas; calcium carbonate; calcium sulphate; ammonium sulphate; synthetic silicon oxides and synthetic calcium silicates or aluminium silicates; elements such as carbon and sulphur; natural and synthetic resins such as coumarone resins, polyvinyl chloride, and styrene polymers and copolymers; solid polychlorophenols; bitumen; waxes beeswax or paraffinwax.

Suitable liquid carriers include water, alcohols such as isopropanol or alcohol; ketones such as acetone, methyl ethyl ketone, methyl isopropy ketone or cyclohexanone; ethers; aromatics such as benzene, xylene, toluene; petroleum fractions such as kerosene or mineral oils, chlorinated aliphatic hydrocarbons such as carbon tetrachloride, tetrachloride ethylene and or trichloride ethylene. Mixtures of these different liquids generally are often suitable.

The compositions of insecticides and fungicides are often formulated and transported in a concentrated form which is subsequently diluted by the user before application. The presence of small amounts of surfactant facilitates this process of dilution. Thus preferably at least one carrier in a composition according to the invention is a surfactant. For example the composition may contain at least two carriers, at least one of which is a surfactant.

A surfactant may be an emulsifier, a dispersant or a wetting agent; it may be nonionic or ionic. Examples of suitable surfactant include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycol, sorbic alcohol, sucrose or pentaerythritol and condensation products of these esters with ethylene oxide and/or propylene oxide; the condensation products of fatty alcohol or alkyl phenols such as p-octylphenol or p-octylcresol, with ethylene-oxide and/or propylene oxide; sulphates or sulphonates of these condensation products; alkaline metal salts or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as sodium dodecylbenzene sulphonate.

Examples of compositions and formulations according to the invention are wettable powder, dustable powder, granule, aqueous solution, emulsifiable concentrate, emulsion, suspension concentrate, aerosol composition and fumigant. Wettable powder usually contains 25, 50 or 75% weight (ab.w) of active ingredient and usually contain in addition to solid inert carrier, 3-10% w of a dispersant and, where necessary, 0-10% w of stabiliser(s) and/or other additives such as penetrants or stickers. Dustable powder are usually formulated as a dust concentrate having a similar composition to that of a wettable powder but a dispersant, and are further diluted with solid carrier to give a composition usually containing 0.5-10% weight of active ingredient. Granules are usually prepared to have a size between 10 and 100 BS mesh (1.676-0.152 mm), and may be manufactured by agglomeration or impregnation techniques. Generally, granules contain 0.5-75% w active ingredient and 0-10% weight of additives such as stabilisers, surfactants, slow release modifiers. The so-called "dry flowable powders" consist of relatively small granules having a relatively high concentration of active ingredient. Emulsifiable concentrates usually contain, in addition to a solvent and, when necessary, co-solvent, 1-50% weight/volume (w/v) active ingredient, 2-20% w/v emulsifiers and 0-20% w/v of other additives such as stabilisers, penetrants and corrosion inhibitors. Suspension concentrates are usually contain 10-75% w active ingredient, 0.5-15% w of dispersing agents, 0.1-10% w of other additives such as defoamers, corrosion inhibitors, stabilisers, penetrants and stickers.

Aqueous dispersant and emulsions, for example compositions obtained by diluting a wettable powder or a concentrate according to the invention with water, also lie within the scope of the invention. The said emulsions may be of the water-in-oil or of the oil-in-water type.

The composition to which one or more other fungicides are added has wider spectrum activity than single compound having general formula (I). In addition, other fungicides may have synergistic effect on the fungicidal activity of the compound having general formula (I). The compound having general formula (I) can also be used with other insecticides, or with another fungicide and other insecticides simultaneously.

DESCRIPTION OF THE INVENTION

The following example are illustrative of the invention, but without being restricted thereby.

Preparation Example

Example 1

Preparation of Compound 1

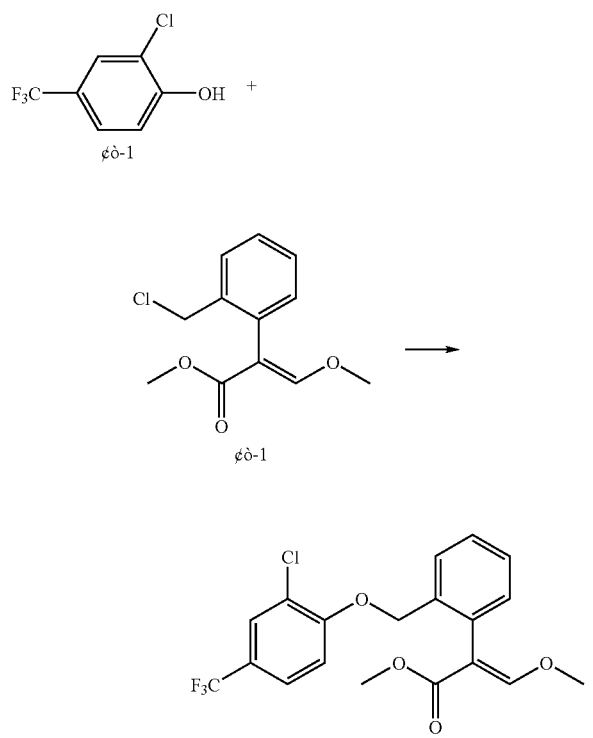

0.8 g dry potassium carbonate, 0.39 g (II-1), 0.4 g (III-1) were dissolved in 20 ml DMF under room temperature, then the solution was heated to reflux. 5 hr later the reaction mixture was poured into crushed ice and extracted with ethyl acetate 3 times. The extractions was united, washed with saturated salt water 3 times, dried, filtrated and condensed under vacuum pressure. The pale yellow solid was obtained as crude product. This was subjected to silica gel column chromatography using a 1:8 (volume/volume) mixture of ethyl acetate and petroleum ether (boiling range: 60-90° C.) as the eluting solution to obtain 0.51 g of compound 1 with m.p. 104-106° C. The yield was 70.5%.

NMR spectrum ($^1$HNMR, 300 MHz, internal standard: TMS, CDCl$_3$) is as follows:

δ ppm 3.71 (3H, s), 3.83 (3H, s), 5.12 (2H, s), 6.89 (1H, d), 7.20 (1H, t), 7.35 (3H, m), 7.53 (1H, m), 7.62 (2H, s).

Example 2

Preparation of Compound 4

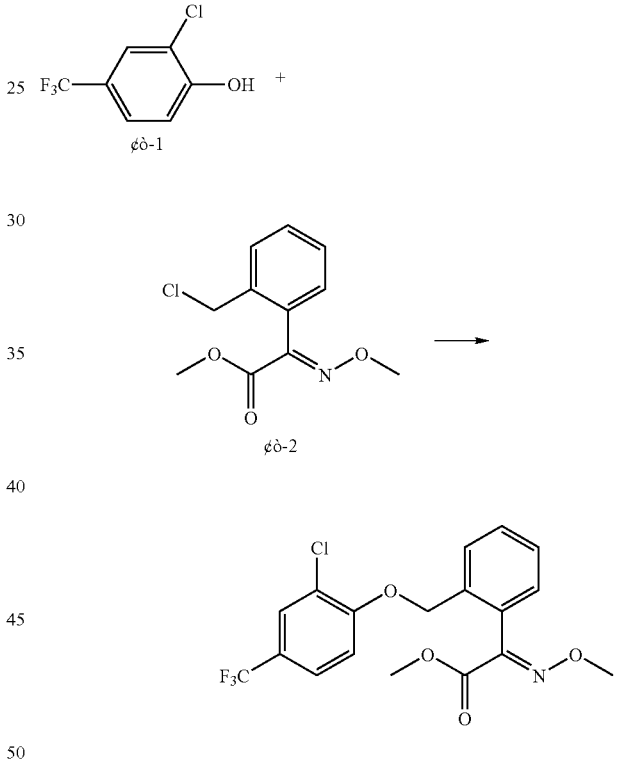

0.8 g dry potassium carbonate, 0.39 g (II-1), 0.42 g (III-2) were dissolved in 20 ml DMF under room temperature, then the solution was heated to reflux. 5 hr later the reaction mixture was poured into crushed ice and extracted with ethyl acetate 3 times. The extraction was united, washed with saturated salt water 3 times, dried, filtrated and condensed under vacuum pressure. The pale yellow solid was obtained as crude product. This was subjected to silica gel column chromatography using a 1:8 (volume/volume) mixture of ethyl acetate and petroleum ether (boiling range: 60-90° C.) as the eluting solution to obtain 0.53 g of compound 1 with m.p. 115-116° C. The yield was 73.2%.

NMR spectrum ($^1$HNMR, 300 MHz, internal standard: TMS, CDCl$_3$) is as follows:

δ ppm 3.88 (3H, s), 4.04 (3H, s), 5.09 (2H, s), 6.93 (1H, d), 7.22 (1H, d), 7.45 (3H, m), 7.58 (1H, d), 7.63 (1H, s).

Example 3

Preparation of Compound 7

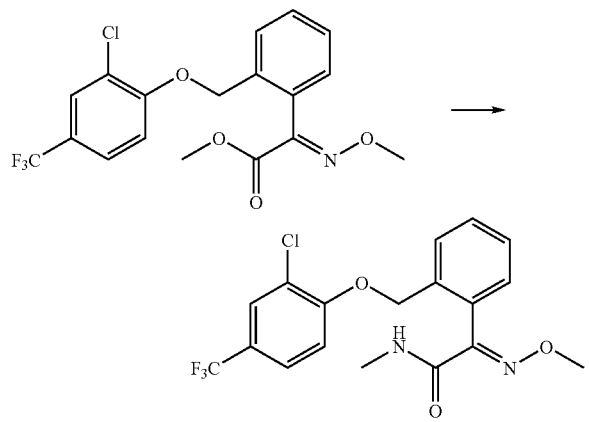

0.60 g compound 4 and water solution of methylamine at molar ratio of 2 were dissolved in 50 ml THF under room temperature. It was stirred overnight. The reaction mixture was extracted with ethyl acetate 2 times after condensed. The extraction was united, washed with water 3 times and saturated salt water 2 times, dried, filtrated and condensed under vacuum pressure. 0.53 g target compound was obtained with m.p. 92-94° C. The yield was 88.5%.

NMR spectrum ($^1$HNMR, 300 MHz, internal standard: TMS, CDCl$_3$) is as follows:

δ ppm 2.92 (3H, s), 3.92 (3H, s), 5.12 (2H, s), 6.95 (1H, d), 7.24 (1H, m), 7.42 (3H, m), 7.54 (1H, d), 7.62 (1H, s).

Other compounds were prepared according the above examples.

NMR spectrum ($^1$HNMR, 300 Hz, internal standard: TMS, CDCl$_3$) of some compounds of this invention are as follows:

Compound 10: oil. δ ppm 3.75 (3H, s), 3.83 (3H, s), 5.24 (2H, s), 7.02 (1H, d), 7.42 (4H, m), 7.66 (2H, t).

Compound 16: m.p. 142-144° C. δ ppm 3.61 (3H, s), 3.77 (3H, s), 6.40 (1H, s), 7.20 (1H, d), 7.35 (3H, m), 7.49 (1H, s), 7.61 (1H, d), 7.76 (1H, d), 8.39 (1H, s).

Formulation Example

Base on 100% active ingredient (weight/weight %)

Example 4

60% Wettable Powders

| | |
|---|---|
| Compound 1 (97.2%) | 60% |
| Sodium dodecylnaphthalenesulfate | 2% |
| Sodiumlignosulfonate | 9% |
| Kaolin | complement to 100% |

All the solid components Compound 1, Sodium dodecylnaphthalenesulfate, Sodiumlignosulfonate, Kaolin are well mixed and shattered until the particle size reaches the standard.

Example 5

35% Emulsion Concentrate

| | |
|---|---|
| Compound 4 (98.4%) | 35% |
| Phosphorous acid | 10% |
| Ethylenoxy aliphatic acid glycerin ester | 15% |
| Cyclohexanone | complement to 100% |

Phosphorous acid is dissolved in cyclohexanone, then the compound 4 and ethylenoxy aliphatic acid glycerin ester are added, the emulsifiable in transparent solution is obtained finally.

Example 6

30% Aqueous Suspension

| | |
|---|---|
| Compound 7 (96.4%) | 30% |
| Sodium dodecylnaphthalenesulfate | 4% |
| Hemicellulose | 2% |
| Epoxypropane | 8% |
| Water | complement to 100% |

The mixture of compound 7, 80% of the amount of water should being added and sodium dodecylnaphthalenesulfate are shattered in a mill (1 mm ball). Other components Hemicellulose and Epoxypropane are dissolved in the rest 20% water, and are added under stirring to obtain 30% aqueous suspension.

Example 7

25% Suspension Emulsifier

| | |
|---|---|
| Compound 10 (96.2%) | 25% |
| Dodecyl polyethylene phosphate ester | 4% |
| Ethylenoxy aliphatic acid glycerin ester | 2% |
| Calcium dodecylbenzenesulfate | 1.5% |
| Polyethylenoxyalkyl propyl ether | 2.5% |
| Cyclohexanone | 30% |
| Petroleum fractions | complement to 100% |

Compound 10 is dissolved in 80% of the amount of solvent (Cyclohexanone and Petroleum fractions) should being added, and then emulsifiers (Dodecyl polyethylene phosphate ester, Ethylenoxy aliphatic acid glycerin ester and Calcium dodecylbenzenesulfate) and dispersant (Polyethylenoxyalkyl propyl ether) are added, the mixture is stirred completely and shattered in a mill (1 mm ball). Other 20% solvents are added.

Biological Testing

Example 8

Determination of Fungicidal Activity

Determination of fungicidal activities against epiphyte diseases by using selected compounds of the invention were carried out by following procedure:

Technical samples were dissolved in a small amount of acetone and diluted to required concentration with water containing 0.1% tween 80. Protective activity was carried out by the following procedure: Test solution was sprayed onto potted plant. Pathogen inoculation was carried out after 24 hours then plants were hold in growth chambers containing constant temperature and moisture for effect. When untreated plant was under desirable disease severity (after 1 week approximately), assessment were carried out by visual observation. Therapy activity was carried out by following procedure: Pathogen inoculation was carried out then test solution was sprayed onto potted plant after 4 days. When untreated plant was under desirable disease severity (3-4 days) assessment were carried out by visual observation.

Part of the test results (dosage based on effective ingredient):

At 400 mg/L, compound 1, 4, 7 showed 100% control against cucumber downy mildew (*Pseudoperonospora cubenis*).

At 400 mg/L, compound 1, 4, 7, 10, 16 showed 100% control against wheat powdery mildew (*Blumeria graminis*).

At 200 mg/L, compound 1, 4, 7 showed 100% control against wheat powdery mildew; compound 10 showed more than 95% control against wheat powdery mildew.

At 200 mg/L, compound 1, 4, 7 showed more than 95% control against wheat root rot (*Helminthosporium sativum*), cucumber anthracnose (*Colletotrichum lagenarium*), wheat glume blotch root rot (*Septria nodrum*), wheat leaf rust (*Puccinia tritici*), rice blast (*Pyricularia oryzae*).

At 12.5 mg/L, compound 1, 4, 7 showed 100% control against wheat powdery mildew.

The comparison between the compounds 1, 4, 7 and kresoxin-methyl (50% suspension, BASF) can see Table 2. The compound 1 therapy activity against wheat powdery mildew can see Table 3.

Example 9

Determination of Insecticidal and Acaricidal Activity

Determination of insecticidal and acaricidal activities against insects and acaricides by using selected compounds of the invention were carried out by following procedure:

Technical samples were dissolved in acetone/methanol (1:1) and diluted to required concentration with water containing 0.1% of tween 80.

Armyworm (*Leucania separata*), diamondback moth (*Plutella xylostella*) culex mosquitoes (*Culex pippens pallens*), *Myzus persicae* (*Myzus persicae* and Carmine spider mite (*Tetranychus cinnabarinus*) were treated with Airbrush spraying tower, and culex mosquito was treated with dipping culture method. The pressure of Airbrush spraying tower was 10 psi (about 0.7 kg/cm2) and the amount of spraying was 0.5 ml. Mortality investigation of test insects was carried out 2 to 3 days after the treatment.

Part of Test Results:

At 600 mg/L, compound 1 showed 100% control of *Myzus persicae*.

t 600 mg/L, compound 1, 4 showed 100% control of Carmine spider mite.

At 150 mg/L, compound 1 showed 100% control of Carmine spider mite.

At 50 mg/L, compound 1 showed 100% control of Carmine spider mite.

At 10 mg/L, compound 1 showed 95% control of Carmine spider mite. The comparison acaricide Pyridaben (The pesticide factory of Jiangshu Jianhu, content 98%) showed 95% control of Carmine spider mite.

TABLE 2

Protective activity against wheat powdery mildew of compounds

| compound | Protective activity % one day | | | | | | | |
|---|---|---|---|---|---|---|---|---|
| | 25 mg/L | 12.5 mg/L | 6.25 mg/L | 3.13 mg/L | 1.56 mg/L | 0.78 mg/L | 0.39 mg/L | 0.19 mg/L |
| 1 | 100 | 100 | 100 | 100 | 100 | 90 | 55 | 30 |
| 4 | 100 | 100 | 100 | 100 | 100 | 98 | 90 | 70 |
| 7 | 100 | 100 | 100 | 100 | 100 | 90 | 85 | 50 |
| kresoxin-methyl | 100 | 100 | 98 | 70 | 40 | 15 | 0 | 0 |

Therapy activity against wheat powdery mildew of compound 1 see table 3.

TABLE 3

Therapy activity against wheat powdery mildew of compound 1

| compound | Therapy activity % 3 days | | | |
|---|---|---|---|---|
| | 12.5 mg/L | 6.25 mg/L | 3.125 mg/L | 1.56 mg/L |
| 1 | 100 | 100 | 80 | 50 |
| kresoxin-methyl | 100 | 20 | 15 | 10 |

We claim:

1. A substituted para-trifluoromethyl phenyl ether compound of formula (I) as follows:

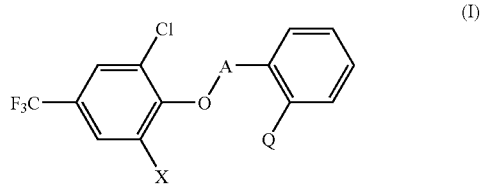

wherein Q is $Q_1$ or $Q_2$

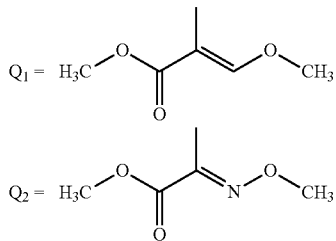

A is $CH_2$;
X is H, halo, CN, $NO_2$, $C_1$-$C_{12}$alkyl, $C_2$-$C_{12}$alkenyl, $C_2$-$C_{12}$alkynyl, $C_1$-$C_{12}$haloalkyl, $C_1$-$C_{12}$alkoxy, $C_1$-$C_{12}$alkylthio, $C_1$-$C_{12}$alkylsulfonyl, $C_1$-$C_{12}$alkylcarbonyl, $C_1$-$C_{12}$alkoxyl $C_1$-$C_{12}$alkyl, $C_1$-$C_{12}$alkoxylcarbonyl, $C_1$-$C_{12}$alkoxylcarbonyl $C_1$-$C_{12}$alkyl, $C_1$-$C_{12}$haloalkoxyl $C_1$-$C_{12}$alkyl, or group is substituted by any other group: amino $C_1$-$C_{12}$alkyl, aroxyl, aryl $C_1$-$C_{12}$alkoxy, aryl, heteroaryl, aryl$C_1$-$C_{12}$alkyl, heteroaryl$C_1$-$C_{12}$alkyl or heteroaryl$C_1$-$C_{12}$alkoxyl;
or a stereoisomer thereof.

2. The substituted compounds according to claim 1, wherein
X is H, halo, CN, $NO_2$, $C_1$-$C_6$alkyl, $C_2$-$C_6$alkenyl, $C_2$-$C_6$alkynyl, $C_1$-$C_6$haloalkyl, $C_1$-$C_6$alkoxy, $C_1$-$C_6$alkylthio, $C_1$-$C_6$alkylsulfonyl, $C_1$-$C_6$alkylcarbonyl, $C_1$-$C_6$alkoxyl $C_1$-$C_6$alkyl, $C_1$-$C_6$alkoxylcarbonyl, $C_1$-$C_6$alkoxylcarbonyl $C_1$-$C_6$alkyl, $C_1$-$C_6$haloalkoxyl $C_1$-$C_6$alkyl, or group is substituted by any other group: amino $C_1$-$C_6$alkyl, aroxyl, aryl $C_1$-$C_6$alkoxy, aryl, heteroaryl, aryl$C_1$-$C_6$alkyl, heteroaryl$C_1$-$C_6$alkyl or heteroaryl$C_1$-$C_6$alkoxyl.

3. The substituted compounds according to claim 2, wherein
X is H, halo, CN, $NO_2$, $C_1$-$C_6$alkyl, $C_2$-$C_6$alkenyl, $C_2$-$C_6$alkynyl, $C_1$-$C_6$haloalkyl, $C_1$-$C_6$alkoxy, $C_1$-$C_6$alkylthio, $C_1$-$C_6$alkylsulfonyl, $C_1$-$C_6$alkylcarbonyl, $C_1$-$C_6$alkoxyl $C_1$-$C_6$alkyl, $C_1$-$C_6$alkoxylcarbonyl, $C_1$-$C_6$alkoxylcarbonyl $C_1$-$C_3$alkyl, $C_1$-$C_3$haloalkoxyl $C_1$-$C_3$alkyl, or group is substituted by any other group: amino $C_1$-$C_3$alkyl, or group is substituted or unsubstituted by any other group: phenyl, phenoxy, benzyl or benzyloxy.

4. The substituted compounds according to claim 3, wherein
X is H, Cl, Br, F, CN, or $C_1$-$C_3$alkyl.

5. A method for preparing a compound according to any one of claims 1-4, which comprises reacting a substituted phenol compound having general formula (II) with a halomethylbenzene having general formula (III) in the presence of a base:

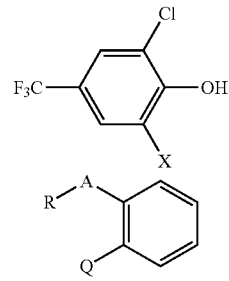

wherein:
R is Cl, Br or I;
Q is $Q_1$ or $Q_2$;

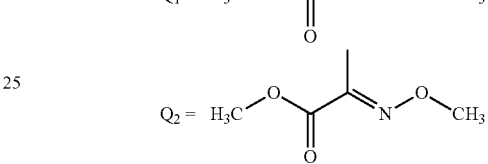

A is $CH_2$;
X is H, halo, CN, $NO_2$, $C_1$-$C_{12}$alkyl, $C_2$-$C_{12}$alkenyl, $C_2$-$C_{12}$alkynyl, $C_1$-$C_{12}$haloalkyl, $C_1$-$C_{12}$alkoxy, $C_1$-$C_{12}$alkylthio, $C_1$-$C_{12}$alkylsulfonyl, $C_1$-$C_{12}$alkylcarbonyl, $C_1$-$C_{12}$alkoxyl $C_1$-$C_{12}$alkyl, $C_1$-$C_{12}$alkoxylcarbonyl, $C_1$-$C_{12}$alkoxylcarbonyl $C_1$-$C_{12}$alkyl, $C_1$-$C_{12}$haloalkoxyl $C_1$-$C_{12}$alkyl, or group is substituted by any other group: amino $C_1$-$C_{12}$alkyl, aroxyl, aryl $C_1$-$C_{12}$alkoxy, aryl, heteroaryl, aryl$C_1$-$C_{12}$alkyl, heteroaryl$C_1$-$C_{12}$alkyl or heteroaryl$C_1$-$C_{12}$alkoxyl.

6. A method of controlling insects in a plant which comprises contacting at least one compound according to claim 1 with the plant.

7. A method of controlling fungi in plant which comprises contacting at least one compound according to claim 1 with the plant.

8. A composition for controlling insects or fungi which comprises at least one compound according to any one of claims 1-4 as an active ingredient, wherein the weight percentage of the active ingredient in the composition is from 0.1% to 99%.

* * * * *